United States Patent [19]

Imai et al.

[11] Patent Number: 4,764,606

[45] Date of Patent: Aug. 16, 1988

[54] 7-FORMYLAMINOCEPHALOSPORIN COMPOUNDS

[75] Inventors: Harumitsu Imai, Kanagawa; Ken-ichi Suzuki, Saitama; Koji Nagai, Tokyo; Shigeru Miyazaki, Saitama; Kenji Abe, Saitama; Isao Takahashi, Saitama; Shigenobu Kadota; Koichi Tanaka, both of Tokyo, all of Japan

[73] Assignee: Yamanouchi Pharmaceutical Co., Ltd., Tokyo, Japan

[21] Appl. No.: 890,906

[22] Filed: Jul. 28, 1986

[30] Foreign Application Priority Data

Aug. 1, 1985 [JP] Japan .................... 60-170408

[51] Int. Cl.$^4$ ................. C07D 501/36; A61K 31/545
[52] U.S. Cl. ..................... 540/221; 514/201; 435/119
[58] Field of Search .................... 540/221; 514/201

[56] References Cited

U.S. PATENT DOCUMENTS 4,609,652 9/1986 Milner et al. .................... 540/221

Primary Examiner—Nicholas S. Rizzo
Attorney, Agent, or Firm—Burgess, Ryan & Wayne

[57] ABSTRACT

A 7-formylaminocephalosporin compound represented by general formula (I):

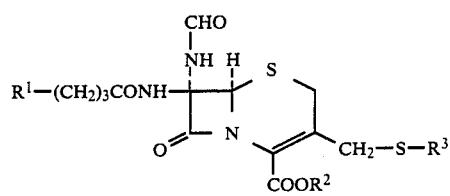

wherein
$R^1$ represents a carboxy group or an aminocarboxymethyl group

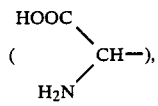

$R^2$ represents a hydrogen atom or a protective group for a carboxy group, and
$R^3$ represents a 5- or 6-membered heterocyclic group which may be substituted;

or a salt thereof, and a process for producing the compound; The compounds are useful intermediates for other cephalosporin compounds having antibacterial activity, and themselves show antibacterial activity, as well.

5 Claims, No Drawings

7-FORMYLAMINOCEPHALOSPORIN COMPOUNDS

FIELD OF THE INVENTION

The present invention relates to novel 7-formylaminocephalosporin compounds and to a process for producing them. The cephalosporin compounds of this invention are useful intermediate compounds for other cephalosporin compounds showing antibacterial activity. The compounds of this invention themselves have antibacterial activity, as well.

DESCRIPTION OF THE PRIOR ART

In Published Unexamined Japanese Patent Application No. 78989/85, it is disclosed that a compound containing a formylamino group at the 7-position on the cephalosporin nucleus, called Chitinovorin, was obtained from bacteria belonging to the genus Flavobacterium. However, this compound is substituted with a hydroxymethyl group at the 3-position thereof and structurally different from the compounds of the present invention. Namely, any compound having the feature as in the compounds of the present invention has not been heretofore known.

SUMMARY OF THE INVENTION

The present invention relates to novel 7-formylaminocephalosporin compounds showing an antibacterial activity and a process for production thereof. More particularly, the present invention relates to cephalosporin compounds containing a formylamino group and a 5-amino-5-carboxyvaleramido group or a 4-carboxybutyramido group at the 7-position thereof and a 5- or 6-membered heterocyclic thiomethyl group which may be substituted, at the 3-position thereof, and a process for producing the compounds by fermentation.

DETAILED DESCRIPTION OF THE INVENTION

The present inventors have separated many microorganisms from the soil and isolated and investigated antibiotics produced from these microorganisms, for the purpose of developing novel antibiotics. As a result, they have found that certain microorganisms can produce 7-formylaminocephalosporin compounds, compounds containing a heterocyclic thiomethyl group directly at the 3-position thereof and can be obtained in a single fermentation step. These compounds are novel and further the microorganisms are new strains belonging to the genus Pseudomonas and products obtained by reacting the thus obtained compounds with D-amino acid oxidase-producing bacteria belonging to the genus Trigonopsis or treated products thereof are also novel compounds.

The compounds of the present invention are novel cephalosporin compounds represented by the general formula (I):

$$R^1-(CH_2)_3CONH-\overset{\overset{CHO}{\underset{}{|}}}{\underset{}{NH}}\overset{H}{\underset{}{\cdot}}\overset{S}{\underset{\underset{COOR^2}{}}{\bigvee_N}}CH_2-S-R^3 \quad (I)$$

wherein
$R^1$ represents a carboxy group or an aminocarboxymethyl group $$(\underset{H_2N}{\overset{HOOC}{\diagdown}}CH-),$$

$R^2$ represents a hydrogen atom or a protective group for a carboxy group, and
$R^3$ represents a 5- or 6-membered heterocyclic group which may be substituted.

Of the compounds represented by general formula (I), compounds ($I_1$) wherein $R^1$ represents an aminocarboxymethyl group $$(\underset{H_2N}{\overset{HOOC}{\diagdown}}CH-)$$

are novel compounds collected by the present inventors from a culture solution obtained by culturing bacteria belonging to the genus Pseudomonas in media supplemented with heterocyclic thiol compounds ($HS-R^3$). Further compounds ($I_2$) wherein $R^1$ represents a carboxy group are novel compounds obtained by reacting the compounds ($I_1$) wherein $R^1$ represents an aminocarboxymethyl group with D-amino acid oxidase-producing bacteria or treated products thereof.

The compounds of the present invention are stable against a variety of $\beta$-lactamases, per se possess antibacterial activity and are not only effective as antibacterial agents but also applicable as raw materials for producing other antibacterial compounds of 7-formylaminocephalosporin type.

An example of the 7-formylaminocephalosporin compound ($I_1$)-producing bacteria belonging to the genus Pseudomonas which are used in the present invention is Pseudomonas sp Y-09069 K strain (deposited in the Fermentation Research Institute under the accession No. FERM BP-1091) separated by the present inventors from the soil in forest as Moroyamamachi, Iruma-gun, Saitama-ken, Japan. Bacteriological properties of the strain are shown below.

(1) Morphology

The cells cultured on bouillon-agar are rods of 0.4 to $0.6 \times 1.0$ to 1.4 μm but show no pleomorphism. No spore is recognized. The cells possess polar flagella and show motility. Gramm staining is negative.

(2) Growth conditions in various media (1) Bouillon-agar medium
Colonies are semi-spherical and gently raised. The edge is smooth and circular. The cells exhibit pale yellow to yellow but no marked viscidity of flagellation. No formation of diffusible pigment is observed.

(2) Bouillon liquid culture
The entire medium becomes turbid, more thickly particularly around the liquid surface.

(3) Bouillon gelatin stab culture
Liquified.

(4) Litmus mil
Positive both in coagulation and in peptonization. The medium becomes acidic.

(3) Physiological properties (1) Reduction of nitrate: weakly positive
(2) Denitration: negative
(3) MR test: negative
(4) VP test: negative
(5) Indole formation: negative
(6) Formation of hydrogen sulfide: negative
(7) Hydrolysis of starch: negative
(8) Utilization of citric acid (Simons medium): negative
(9) Utilization of inorganic nitrogen source: negative
(10) Formation of pigment: Ammonium salts are utilized as only one nitrogen source.
(11) Urease: negative
(12) Oxidase: positive
(13) Catalase: positive
(14) Growth temperature: 10°–30° C.
Optimum growth temperature: 18°–24° C.
Growth pH: 5–8.5
Optimum growth pH: 6–7.5
(15) Growth under anaerobic condition: not grown
(16) OF test: O type
(17) Auxotrophy: none
(18) Decomposition of arginine: negative
(19) Accumulation of poly-$\beta$-hydroxybutyrate in bacterial cell: positive
(20) Growth in bouillon medium supplemented with NaCl: not grown with more than 3%.
(21) Utilizaion of carbon sources
  (a) The following carbonaceous compounds can utilize and grow as only one carbon source.
    Glucose, fructose, trehalose, sucrose, raffinose, D-galactose, maltose, lactose, salicin, citric acid, succinic acid, acetic acid, L-alanine, L-asparagine
  (b) The following carbonaceous compounds cannot be utilized as only one carbon source.
    L-Arabinose, D-xylose, inositol, L-ramnose, mannitol, D-sorbitol, glycerine, L-arginine, L-lysine
(22) Extraction of endobacillary pigment
As a result of analysis, endobacillary yellow pigment was identified to be of phenazine type.

In view of the foregoing bacteriological properties, this strain is a Gramm-negative rod, moves with polar flagella, forms no spore, deposits yellow pigment of phenazine type in the cells, absolutely aerobic and has not particular auxotrophy. It accumulates poly-$\beta$-hydroxybutyrate in the cells and oxidase- and catalase-positive but negative in reductivity of nitrates, decomposition of L-arginine and denitration. Further it can utilize various sugars, amino acids, organic acids, etc. as only one carbon source. It has a growth temperature range of 10° to 33° C. and grows well at pH of 6 to 7.5. As a result of investigations of bacteria having such properties in Bergey's Manual of Determinative Bacteriology, 8th ed., 1975, and Bergey's Manual of Systematic Bacteriology, vol. 11, 1984, the strain has been identified to be a strain belonging to the genus Pseudomonas. However, no bacterium having properties identical with those of this strain is found in known bacteria and therefore, this strain is determined to be a novel strain belonging to the genus Pseudomonas and has been named Pseudomonas sp Y-09069 K strain.

This strain has been deposited at the Fermentation Research Institute in the Agency of Industrial Science and Technology under the accession number FERM BP-1091.

The Y-09069 K strain has been explained as above but as is well known in the art, various properties of a mocrobe are not constant but vary naturally or artificially. As the strains that can be used in the present invention, mention may be made of all bacteria belonging to the genus Pseudomonas which are capable of producing the 7-formylaminocephalosporin compounds. Further the bacteria used in the present invention also include artificial variants having enhanced productivity of the 7-formylaminocephalosporin compounds by treatments such as irradiation with X rays, gamma rays, ultraviolet rays, etc.; treatments with chemical agents for variation, phage contact, transformation, transduction, genetic recombination by conjugation, genetic recombination by cell fusion, gene introduction using plasmid, etc.; or mutants which naturally occur.

(Method for Production)

According to the present invention, the 7-formylaminocephalosporin compound (wherein $R^1$ represents

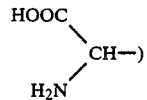

can be produced by culturing the 7-formylaminocephalosporin compound-producing bacteria belonging to the genus Pseudomonas in media supplemented with the heterocyclic thiol compounds (HS—$R^3$) and harvesting the compounds from the culture.

Cultivation is conducted using media containing nutrient sources that the microbe utilize. Any of synthetic, semi-synthetic, natural, solid or liquid media may be used but it is generally preferred to use liquid media containing natural nutrient sources. As the nutrient sources to be supplemented in media, various amino acids and organic acids are used as the carbon source in addition to D-glucose, starch and glycerine; and as the nitrogen source, there may be used organic and inorganic nitrogen sources such as meat extract, peptone, gluten meal, casein hydrolysate, cotton seed lees, soybean powders, peanut powders, fish powders, corn steep liquor, dry yeast, yeast extract, various amino acids (for example, glutamic acid, alanine, lysine, etc.), ammonium salts (for example, ammonium nitrate, ammonium sulfate, etc.), urea, etc.

The media may further be supplemented, if necessary and desired, with sulfates, nitrates, chlorides, carbonates, phosphates, etc. of metals such as sodium, potassium, magnesium, calcium, zinc, iron, etc.

It is preferred to perform cultivation under aerobic conditions. Any of stationary culture, shake culture and aerial agitation culture may be adopted but shake or aerial agitation culture is advantageous. It is preferred that the culture be performed at temperatures ranging from approximately 18° to 30° C., more preferably approximately 24° to 28° C. It is advantageous that pH of the medium be maintained at about 5.5 to about 8.5, particularly in a neutral range of 6 to 8. The culture period varies depending upon composition of medium, culture conditions such as temperature, etc. but generally for about 2 to about 10 days.

Isolation, purification and collection of the desired compound from the culture may be performed by applying ordinary means conventionally used in the art of microbic technology. The desired compound is accumulated mainly in the culture solution and thus isolated and purified from a bacteria-free solution obtained by removing the bacteria by means of centrifugation, filtration, etc.

It is preferred that isolation and purification be performed by applying methods utilizing difference in solubility for suitable solvents, difference in precipitation ability or precipitation speed in a solution, difference in adsorption affinition to various adsorbents, difference in partition in two liquid phases, etc. These methods can be used, if necessary and desired, singly or in combination in optional orders, or repeatedly.

As the heterocyclic thiol compound supplemented in the media in the process by fermentation described above, 5- or 6-membered heterocyclic thiol compounds which may optionally be substituted are employed. In more detail, the heterocyclic thiol refers to a compound containing 1 to 4 hetero atoms selected from, e.g., an oxygen atom, a sulfur atom and a nitrogen atom. As the substituent mention may be made of a straight or branched lower alkyl group having 1 to 5 carbon atoms. Representative examples of these heterocyclic thiol compounds include pyridylthiol, tetrazolylthiol, thiadiazolylthiol and those substituted with a lower alkyl group(s) on these heterocyclic thiols. Specific examples include 4-mercaptopyridine, 3-methyl-4-mercaptopyridine, 5-mercapto-1H-tetrazole, 5-mercapto-1-methyl-1H-tetrazole, 5-mercapto-1,3,4-thiadiazole, 5-mercapto-2-methyl-1,3,4-thiadiazole, etc. These heterocyclic thiol compounds may also be used in the form of appropriate salts thereof. As such salts, mention may be made of inorganic salts such as alkali metal salts, alkaline earth metal salts, ammonium salts, etc.; salts with organic bases such as triethyl amine, triethanolamine, lysine, arginine, etc. If necessary and desired, salts having high solubility in water may be chosen from these salts. Further in case that the heterocyclic thiol compounds have a strong toxicity to the microorganism, they may take the form of salts which are sparingly soluble in water. Furthermore the heterocyclic thiol compound may also be used in such a form, e.g., disulfide derivatives ($R^3$—S—S—$R^3$) of $R^3$—SH, etc. that can be changed to the desired heterocyclic thiol compound during culture.

Some of the thus obtained compounds ($I_1$) (wherein $R^1$ represents

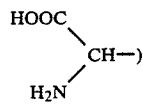

are described below. These compounds takes an α-configuration with the formylamino group at the 7-position thereof and a β-configuration with the acid amido group at the other 7-position thereof. Further these compounds may be harvested not only in the form of a free acid but also in the form of salts (alkali metal salts such as sodium salts, potassium salts, etc.; alkaline earth metal salts such as calcium salts, magnesium salts, barium salts, etc.; organic amine salts such as triethyl amine salts, diethanolamine salts, piperidine salts, morpholine salts, etc.) or esters thereof.

(1) 7-(5-Amino-5-carboxyvaleramido)-7-formylamino-3-(1-methyl-1H-tetrazol-5-yl)thiomethyl-3-cephem-4-carboxylic acid

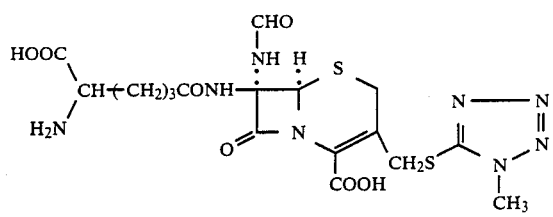

Heterocyclic thiol compound supplemented:
5-Mercapto-1-methyl-1H-tetrazole (2) 7-(5-Amino-5-carboxyvaleramido)-7-formylamino-3-(pyridin-4-yl)thiomethyl-3-cephem-4-carboxylic acid

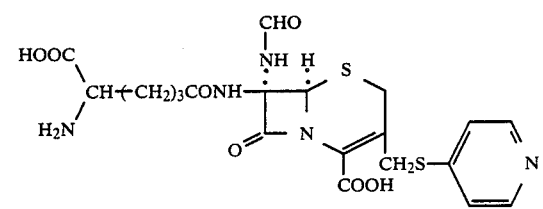

Heterocyclic thiol compound supplemented:
4-Mercaptopyridine (3) 7-(5-Amino-5-carboxyvaleramido)-7-formylamino-3-(5-methyl-1,3,4-thiadiazol-2-yl)thiomethyl-3-cephem-4-carboxylic acid

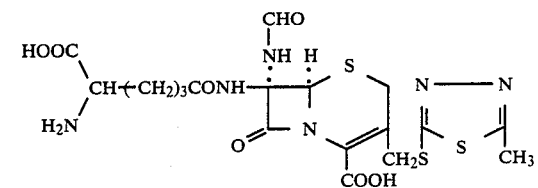

Heterocyclic thiol compound supplemented:
2-Mercapto-5-methyl-1,3,4-thiadiazole

Next, among the compounds of the present invention, Compound ($I_2$) wherein $R^1$ represents a carboxy group can be produced by reacting the thus obtained Compound ($I_1$) wherein $R^1$ is an aminocarboxymethyl group with cells of D-amino acid oxidase-producing bacteria belonging to the genus Trigonopsis or treated products thereof under aerial conditions. The D-amino acid oxidase-producing bacteria belonging to the genus Trigonopsis as used herein can be chosen from type culture stored in any bacteria stock authorities or may be classified from the natural world. Further for purposes of enhancing an activity of producing Compound ($I_2$), variants obtained from the above-described strain in a conventional manner may also be advantageously used in the present invention.

As a microorganism having the above-described D-amino acid oxidase activity, Trigonopsis variabilis may be illustrated. This strain is accessible as Strain Nos. IFO 0755 and IFO 0671 from the Fermentation Institute Foundation. Further bacteriological properties of this strain are described in S. Sentheshanmuganathan, W. J. Nickersion: J. Gen. Microbiol., 27, 437–449 (1962).

To producing the desired product (I₂) using such microorganisms having the D-amino acid oxidase activity, in general, these microorganisms are first cultured followed by reacting the 7-formylaminocephalosporin compound (I₁) of general formula (I) wherein $R^1$ is an aminocarboxymethyl group with the thus obtained cells or treated products thereof under appropriate conditions. As methods for cultures to obtain the cells, aerial culture is generally desired; preferably culture is performed by liquid aerial agitation culture. As compositions for media, media conventionally used as media for microorganisms are employed.

Namely, synthetic media, semi-synthetic media or natural media are used. For the medium composition, glucose, sucrose, mannitol, glycerine, dextrine, starch, vegetable oils, etc. are used as carbon sources and as nitrogen sources, meat extract, peptone, gluten meal, cotton seed oil, soybean powders, peanut powders, fish powders, corn steep liquor, dry yeast, yeast extract, ammonium sulfate, urea and other organic or inorganic nitrogen sources are employed. If necessary and desired, sulfates, nitrates, chlorides, carbonates, phosphates, etc. of Na, K, Mg, Ca, Zn, Fe, etc. are supplemented as metal salts. Furthermore, accelerators or defoaming agents such as methionine, cysteine, cystine, methyl oleate, lard, silicone oil, surfactants, etc. may be appropriately used, if necessary and desired.

Good results are obtained when the pH of a medium is kept in a range of approximately 4 to 10, preferably 5 to 6.

Particularly in cases where D-(or DL-)amino acid, for example, D-(or DL-)methionine, D-(or DL-)alanine, D-(or DL-)valine, etc. are incorporated in the medium, excellent activity of the D-amino acid oxidase can be obtained. It is preferred that culture temperature be at 18° to 37° C., more preferably about 30° C. The culture period may vary depending upon culture condition, particularly culture apparatus, medium composition, culture temperature, etc. but it is preferred that the period be decided so as to complete the culture at the time when the activity of the D-amino acid oxidase indicates the maximum; generally 2 to 10 days are appropriate.

The thus obtained cells or treated products thereof are used for oxidation of D-amino acids of the starting material (I₁). The treated products of the cells as used herein refer to the products obtained by appropriate treatment of the cells to convert the cells into a form capable of enhancing the D-amino acid oxidase activity and advantageous for the production of the desired product (I₂). For example, the activity of the D-amino acid oxidase in the present invention is present generally within the cells. Therefore, the treated products refer to a cell-free extract obtained by applying any physical or chemical means to the cells collected from the culture of the D-amino acid oxidase-producing bacteria followed by washing, a partially purified product obtained by applying any known method for separating and purifying enzyme from the cell-free extract, activated cells obtained by subjecting D-amino acid oxidase activity or cells having bound to water-insoluble high molecular substance or inorganic carrier by physical or chemical means, after partial purification or purification, to any activated treatment, etc.

In the present invention, practical use is limited with the aforesaid soluble enzyme in its production and repeated use. Therefore, the use of insoluble enzyme such as activated enzyme is advantageous in view of recovery and repeated use.

The aforesaid treatment for activating the cells can be performed by imparting to the cells a certain mild injury to such a degree as not causing any disintegration. Examples of these treatments for activation include a method which comprises freezing the cells at 10° C. or lower in an acidic pH range, e.g., pH of about 3 to about 4 and then thawing; a method which comprises treating the cells in an aqueous phase together with one or more organic solvents, e.g., acetone, n-butanol, 2-phenylethanol, dimethyl ether, cyclohexane, benzene, toluene, etc.; a method which comprises treating the cells with 0.1 to 10% of a surfactant, for example, an aqueous solution of a cationic surfactant such as cetyl trimethyl ammonium, cetyl pyridinium, cetyl dimethylbenzyl ammonium hydride, etc.; an anionic surfactant such as dodecyl sulfate, alkyl-aryl-sulfonic acid alkali metal salts, sodium deoxycholate, etc.; a non-ionic surfactant such as sorbitan monolaurate, Triton X-100, etc.; a method which comprises treating the cells with a diluted solution of potassium hydroxide or sodium hydroxide; a method which comprises suspending in a solution having high osmosis, e.g., in a 2M sucrose solution and then rapidly diluting with water; etc. These treatments for activation may vary depending upon various factors such as temperature, treating time, pH, concentration of reagent, etc. and it is thus necessary to appropriately determine the optimum conditions for activation.

Further in case that the action of catalase normally co-present in the cells is not inhibited, oxidative decarboxylation into the desired product (I₂) is incomplete so that 7-(5-carboxy-5-oxovaleramido)-7-formylaminocephalosporin derivatives represented by general formula:

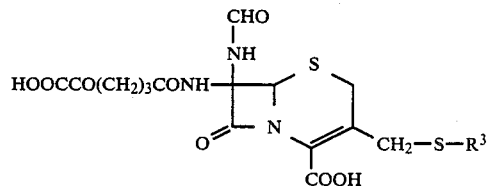

are by-produced. Accordingly, to produce the desired product (I₂) selectively, it is desired to inhibit the action of catalase. Suitable examples of catalase inhibitors include ascorbic acid, 3-amino-1,2,3-triazole and alkali metal azides. Sodium azide is particularly preferred.

This inhibitor may be incorporated in the reaction mixture during conversion of the starting material (I₁) to the desired product (I₂); alternatively, instead of using the inhibitor in the aforesaid conversion, the cells may also be pretreated with the inhibitor. Sodium azide is used in an amount of approximately 1 to 100 mM. Alternatively, catalase in the cells described above can also be inactivated by heat treatment prior to using the cells in the aforesaid conversion step. Namely, the above-described cells are treated at 40° to 60° C., preferably at about 50° C. for at least 3 hours so that the catalase activity decreases markedly but on the other hand, the D-amino acid oxidase activity remains as it is. This heat treatment can also be subjected to the cells in a simple aqueous or buffer suspension but it is particularly advantageous that the cells be treated so as to undergo treatment with an agent for activation at the same time when the cells are treated. For example, the treatment for activation is performed at 50° C. for 4 hours using toluene as a solvent, whereby inhibition of the catalase activity and the aforesaid cell activation can be achieved simultaneously.

The reaction of enzyme system of the aforesaid activated cells with starting material ($I_1$) is generally performed at pH of 6 to 8. It is desired that the reaction be performed at temperatures of 30° to 40° C. The reaction time may be varied mainly depending upon enzyme titer but generally 1 to 5 hours.

The above-described enzyme reaction is performed under aerial conditions and therefore it is preferred to conduct the reaction generally under aeration or by passing oxygen.

As described hereinabove, the starting material ($I_1$) is extracted from a fermentation broth only with difficulty due to its amphoteric structure. According to the process of the present invention, however, the above-described enzyme reaction can be carried out under appropriate conditions after removing the cells in a fermentation broth of the starting material ($I_1$) and, the formed desired product ($I_2$) can easily be recovered by extraction with a solvent or adsorption to ion exchange resin. The reaction solution is adjusted to an acidic range, e.g., pH of 2.5 or less, from which the product can be extracted with an appropriate organic solvent, for example, ethyl acetate, n-butanol, etc. Further the use of ion exchange resin and the extraction with a solvent in combination gives good results. An appropriate ion exchange resin is liquid amine anionic ion exchange resin. Preferred examples of the solvent include ethyl acetate, butyl acetate, n-butanol, etc. Further it is also possible to separate using solid ion exchange resin. In this case, an appropriate solvent can easily be determined through preliminary experiment.

To further purify and obtain the pure product, methods conventionally used for purification of antibiotics are employed.

The desired product ($I_2$) can be harvested not only in the form of its free acid but also as ordinary alkali metal salts, alkaline earth metal salts, organic amine salts, etc. Representative examples of the compound ($I_2$) obtained according to the process of the present invention are as follows.

(a) 7-(4-Carboxybutyramido)-7-formylamino-3-(1-methyl-1H-tetrazol-5-yl)thiomethyl-3-cephem-4-carboxylic acid

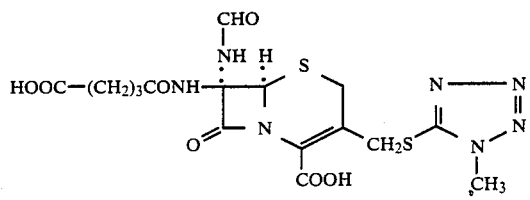

(b) 7-(4-Carboxybutyramido)-7-formylamino-3-(pyridin-4-yl)thiomethyl-3-cephem-4-carboxylic acid

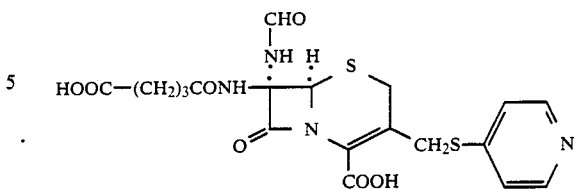

(Effects of the Invention)

The desired compounds of the present invention exhibit antibacterial activity against Gram-negative bacteria and slime molds. Further the compounds are characterized in that they are extremely stable against various β-lactamases. Next, the antibacterial activity of a representative example of the compounds of the present invention is shown below. Measurement of antibacterial activity:

Water is added to the compound obtained in Example 1 to make a solution. The solution is impregnated with a thin paper disc (made by Toyo Engineering Works, Ltd.) having a 8 mm diameter for measurement of antibacterial activity. After an excess of the solution is removed, the disc is dried and paper disc assay is performed using various specimen bacteria. A diameter (mm) of inhibition zone is measured with the bacteria at 37° C. 16 hours after. The composition of the medium comprises 1.0% of polypeptone, 0.1% of yeast extract and 1.2% of agar (made by Difco Co., Ltd.) at pH of 7.0.

Results

| Specimen Bacteria | Diameter of Inhibition Zone (mm) |
|---|---|
| Proteus sp. ss-12 (highly sensitive to β-lactam) | 33.5 |
| Escherichia coli NIHJ | 10.0 |
| Klebsiella pneumoniae ATCC 10031 | 14.0 |

The desired compounds (I) or salts of the present invention may be administered orally or parenterally. In this case, the compounds may be orally administered in the form of tablets, capsules, powders, etc. using vehicles, stabilizers, preservatives, wetting agents, surfactants, etc. conventionally used, or may also be parenterally administered in the form of injections, ointments, suppositories, etc.

Dosage may be appropriately varied depending upon object to be administered, therapeutic purpose, etc.

(Examples)

Next, the compounds and their production in accordance with the present invention will be described in more detail with reference to the examples below.

Example 1

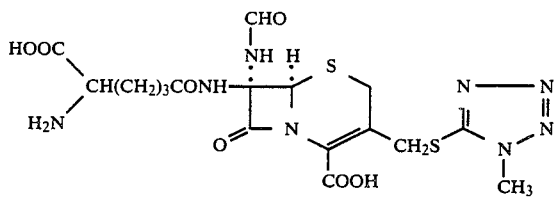

A medium (pH 7.0) containing 3.0% of potato starch, 1.5% of soybean powders, 0.2% of loast jam, 0.25% of soybean oil and 0.25% of sodium chloride was prepared and each aliquot of 60 ml was charged in a 500 ml Erlenmeyer's flask followed by sterilization at 120° C. for 20 minutes. The cells of Pseudomonas sp. Y-09069 K strain grown on bouillon agar medium was scraped and inoculated on this medium and, shake cultured at 28° C. for 48 hours to make a seed culture solution. Next, 15 liters of a medium supplemented with 0.1% of 5-mercapto-1-methyl-1H-tetrazole (sodium salt) to the above-described medium was charged in a stainless-made fermenter of a 20 liter volume and the seed culture solution was inoculated thereon in a ratio of 3.0%. Culture was continued for 72 hours at a temperature of 28° C. in an aerial amount of 15 liters/min at 220 r.p.m., whereby the antibacterial activity became maximum against Proteus sp. SS-12 strain. 1N Hydrochloric acid was added to the thus-obtained culture solution to adjust pH to 5.0. Thereafter the culture solution was centrifuged to remove the cells. Thus 12 liters of the supernatant was obtained. After adjusting pH to 4.5, the supernatant was passed through a column filled up with activated charcoal (1 liter). After washing the column with water (2 liters), the antibacterial active substance was eluted with 50% acetone-water (5 liters). After the eluate was concentrated to 2 liters at 40° C. under reduced pressure, the concentrate was adjusted to pH of 4.5 and passed through a column of Dowex 1×2 (Cl⁻ type, 100 ml) (manufactured by The Dow Chemical Co., Ltd.). After washing the column with water (300 ml), the antibacterial active substance was eluted with a 5% aqueous sodium chloride solution (300 ml). After adjusting pH to 4.5, the eluate was passed though a column filled up with activated charcoal (50 ml). After washing the column with water (100 ml), the antibacterial active substance was eluted with 50% acetone-water (200 ml). After the eluate was concentrated to 100 ml at 40° C. under reduced pressure, the concentrate was adjusted to pH of 4.5 and passed through a column filled up with DEAE-Sephadex A-25 (phosphate type, 35 ml) (Pharmacia Fine Chemical Co., Ltd.). After washing the column with water (70 ml), the antibacterial active substance was eluted and fractionated by the linear concentration gradient method. Effective fractions (50 ml) were collected. After adjusting pH to 4.5, the fractions were passed through a column packed with activated charcoal (50 ml). After washing the column with water (40 ml), the antibacterial active substance was eluted with 50% acetone-water. After adjusting pH to 7.0, the eluate was concentrated to 10 ml at 40° C. under reduced pressure and freeze dried to give pale yellow powders (120 mg). The pale yellow powders (120 mg) were subjected to high speed liquid chromatography for fractionation using Zorbax BP-NH$_2$ (10 $\phi \times$250 mm, made by Du Pont Co., Ltd.) as carriers followed by elution and fractionation with a 0.02M phosphate buffer solution (pH 6.5).

Each fraction was subjected to analysis by means of high speed liquid chromatography using Zorbax BP-NH$_2$ (4.3 $\phi \times$300 mm, made by Du Pont Co., Ltd.) under conditions of 0.02M phosphate buffer solution (pH 6.5), flow speed of 1 ml/min and detection at 260 nm to collect fractions showing a single peak at 8.4 mins. and showing antibacterial activity against Proteus sp. SS-12. After adjusting pH to 4.5, the effective fractions (5 ml) was passed through a column packed with activated charcoal (2 ml). After washing with water (10 ml), elution was performed with 50% acetone-water (10 ml). After adjusting pH to 7.0, the eluate was concentrated to 2 ml at 40° C. under reduced pressure and then freeze dried to give white powders (5 mg) of 7-(5-amino-5-carboxyvaleramido)-7-formylamino-3-(1-methyl-tetrazol-5-yl)thiomethyl-3-cephem-4-carboxylic acid. This compound shows the following physicochemical properties.

(1) UV absorption spectrum: UV absorption spectrum in a 0.02M phosphate buffer solution (pH 6.5): absorption maximum; about 200 nm and about 265 nm.

(2) IR absorption spectrum: Major absorptions appear at 3400–3200, 1770–1780, 1670–1600, 1510 and 1400 cm$^{-1}$ in the potassium bromide tablet method.

(3) NMR spectrum: Characteristic major signals appear at 4.07 (3H, singlet), 5.32 (1H, singlet) and 8.16 (1H, singlet) of δ value (ppm) in NMR spectrum of 400 MHz in heavy water.

(4) Mass spectrum: In FAB-MS, 515 (MH+) and 537 (M+Na+) are observed.

(5) Classification of substance: amphoteric substance (6) Appearance: white powder (7) Hydrolysis with 6N hydrochloric acid gives α-aminoadipic acid.

(8) Solubility: easily soluble in water, hydrated acetone and hydrated alcohol (9) Paper chromatography:
Toyo Filter Paper No. 514A (manufactured by Toyo Filter Paper Co., Ltd.)
Solvent system. 66% acetonitrile water Rf=0.26

(10) High speed liquid chromatography:
Carrier—Zorbax BP-NH$_2$, made by Du Pont Co., Ltd.) 4.3 $\phi \times$300 mm
Moving phase—0.02M monosodium phosphate aqueous solution, adjusted pH to 6.5 with 1N sodium hydroxide
Flow rate—1 ml/min
Detection—260 nm
Retention time—8.4 mins.

Example 2

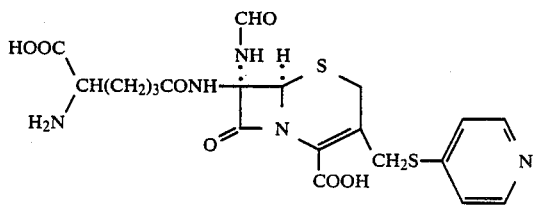

Pale yellow powders, 150 mg, prior to subjecting to high speed liquid chromatography for fractionation using Zorbax BP-NH$_2$ were obtained in a manner similar to Example 1 except that 4-mercaptopyridine was supplemented to the medium in place of 5-mercapto-1-methyl-1H-tetrazole (sodium salt).

The pale yellow powders were subjected to high speed liquid chromatography for fractionation using Zorbax BP-NH$_2$ as carriers under conditions similar to Example 1. Then, 10 ml of effective fractions showing a single peak at 11.2 mins. and showing antibacterial activity against Proteus sp. SS-12 was collected. Thereafter the fractions were treated in a manner similar to Example 1 to give 10 mg of white powders of 7-(5-amino-5-carboxyvaleramido)-7-formylamino-3-(pyridin-4-yl)thiomethyl-3-cephem-4-carboxylic acid.

This compound shows the following physico-chemical properties.

(1) UV absorption spectrum: UV absorption spectrum in a 0.02M phosphate buffer solution: absorption maximum; about 200 nm and about 270 nm.

(2) IR absorption spectrum: Major absorptions appear at 3400-3200, 1770-1780 and 1670-1600 cm$^{-1}$ in the potassium bromide tablet method.

(3) NMR spectrum: Characteristic major signals appear at 5.25 (1H, singlet), 7.44 (2H, doublet, J=4.88 Hz), 8.15 (1H, singlet) and 8.36 (2H, broad) of δ value (ppm) in NMR spectrum of 400 MHz in heavy water.

(4) Mass spectrum: In FAB-MS, 510 (MH$^+$) and 532 (M+Na$^+$) are observed.

(5) Classification of substance: amphoteric substance (6) Appearance: white powder (7) Hydrolysis with 6N hydrochloric acid gives α-aminoadipic acid.

(8) Solubility: easily soluble in water, hydrated acetone and hydrated alcohol (9) Paper chromatography:
Toyo Filter Paper No. 514A (manufactured by Toyo Filter Paper Co., Ltd.)
Solvent system—n-butanol: acetic acid:water (4:1:2) Rf=0.14

(10) High speed liquid chromatography:
Carrier—Zorbax BP-NH$_2$ (made by Du Pont Co., Ltd.) 4.3 φ×300 nm
Moving phase—0.02M monosodium phosphate, aqueous solution, adjusted pH to 6.5 with 1N sodium hydroxide
Flow rate—1 ml/min
Detection—260 nm
Retention time—11.2 mins.

Example 3

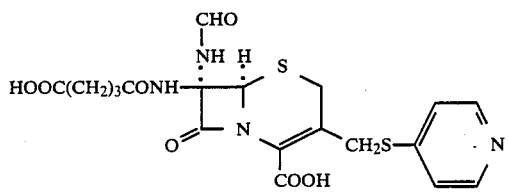

7-(5-Amino-5-carboxyvaleramido)-7-formylamino-3-(pyridin-4-yl)thiomethyl-3-cephem-4-carboxylic acid obtained in Example 2 was diluted to make a solution showing the inhibition zone diameter of 20 mm against Proteus sp. SS-12 by the paper disc method. The solution was adjusted to pH of 7.5. To 30 μl of the solution were added 12 μl of a 1% aqueous hydrogen peroxide solution, 12 μl of a 1% sodium azide aqueous solution and 18 μl of a solution obtained by diluting D-amino acid oxidase derived from Trigonopsis variabilis (IFO 0755, IFO 0671, cf. U.S. Pat. No. 4,242,449) with a 0.02M phosphate buffer solution (pH 7.0) in 40,000 units/ml. The thus obtained solution was reacted at 37° C. for 1 hour to give 7-(4-carboxybutyramido)-7-formylamino-3-(pyridin-4-yl)thiomethyl-3-cephem-4-carboxylic acid.

This compound shows the following physico-chemical properties.

(1) High speed liquid chromatography:
Carrier—Zorbax BP-NH$_2$, 4.3 φ×300 mm
Moving phase—0.02M-NaH$_2$PO$_4$, pH 6.5
Flow rate—1 ml/min
Detection—260 nm
Retention time—19.2 mins.

We claim:

1. A 7-formylaminocephalosporin compound represented by formula (I):

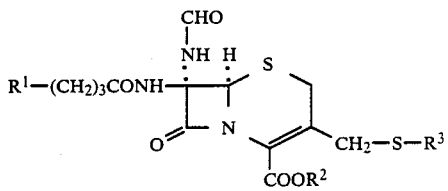

wherein
R$^1$ represents a carboxy group or an aminocarboxymethyl group

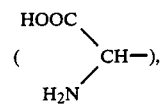

R$^2$ represents a hydrogen atom or a protective group for a carboxy group, and
R$^3$ represents a 5- or 6-membered heterocyclic group which may be substituted and has 1 to 4 hetero atoms selected from the group consisting of an oxygen atom, a sulfur atom and a nitrogen atom; or a pharmaceutically acceptable salt thereof.

2. The 7-formylaminocephalosporin compound or a salt thereof according to claim 1 wherein R$^3$ represents a pyridyl group, a tetrazolyl group or a thiadiazolyl group which three groups may be substituted with a lower alkyl group or lower alkyl groups.

3. The 7-formylaminocephalosporin compound or a salt thereof according to claim 1 which is 7-(5-amino-5-carboxyvaleramido)-7-formylamino-3-(1-methyltetrazol-5-yl)thiomethyl-3-cephem-4-carboxylic acid.

4. The 7-formylaminocephalosporin compound or a salt thereof according to claim 1 which is 7-(5-amino-5-carboxyvaleramido)-7-formylamino-3-(pyridin-4-yl)thiomethyl-3-cephem-4-carboxylic acid.

5. The 7-formylaminocephalosporin compound or a salt thereof according to claim 1 which is 7-(4-carboxybutyramido)-7-formylamino-3-(pyridin-4-yl)thiomethyl-3-cephem-4-carboxylic acid.

* * * * *